(12) United States Patent
Narayanan et al.

(10) Patent No.: US 11,666,269 B2
(45) Date of Patent: Jun. 6, 2023

(54) SLEEPING MASK METHODS AND PANELS WITH INTEGRATED SENSORS

(71) Applicant: International Business Machines Corporation, Armonk, NY (US)

(72) Inventors: Rajeev Narayanan, Briarcliff Manor, NY (US); Bing Dang, Chappaqua, NY (US); Jenna Reinen, Greenwich, CT (US); Jeffrey L. Rogers, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 386 days.

(21) Appl. No.: 16/874,036

(22) Filed: May 14, 2020

(65) Prior Publication Data

US 2021/0353219 A1 Nov. 18, 2021

(51) Int. Cl.
| | | |
|---|---|---|
| A61B 5/00 | (2006.01) | |
| A61B 5/16 | (2006.01) | |
| A61B 5/01 | (2006.01) | |
| A61B 5/11 | (2006.01) | |
| A61B 5/0531 | (2021.01) | |

(Continued)

(52) U.S. Cl.
CPC .......... *A61B 5/4809* (2013.01); *A61B 5/0059* (2013.01); *A61B 5/01* (2013.01); *A61B 5/0531* (2013.01); *A61B 5/1103* (2013.01); *A61B 5/163* (2017.08); *A61B 5/30* (2021.01); *A61B 5/369* (2021.01); *A61B 5/6803* (2013.01); *A61B 2562/0214* (2013.01); *A61B 2562/0219* (2013.01); *A61B 2562/0257* (2013.01); *A61B 2562/0271* (2013.01); *A61B 2562/166* (2013.01)

(58) Field of Classification Search
CPC ..... A61B 5/163; A61B 5/1103; A61B 5/6803; A61B 5/369; A61B 5/4809; A61B 5/0531; A61B 5/01; A61B 2562/0219; A61B 2562/166; A61B 2562/0214; A61B 2562/0271; A61B 5/7267; A61B 5/0077; A61B 2562/0257
USPC ....................................................... 600/544
See application file for complete search history.

(56) References Cited

U.S. PATENT DOCUMENTS

2005/0043652 A1\* 2/2005 Lovett ................... A61B 5/1116
600/595
2005/0190065 A1\* 9/2005 Ronnholm ........... G04G 21/025
340/575

(Continued)

FOREIGN PATENT DOCUMENTS

WO WO-8908423 A \* 9/1989 ............. A61B 3/113

OTHER PUBLICATIONS

"A Manual of Standardized Terminology,Techniques and Scoring System for Sleep Stages of Human Subjects." Psychiatry and Clinical Neurosciences, vol. 55, No. 3, 2001, pp. 305-310, onlinelibrary. wiley.com/doi/full/10.1046/i.1440-1819.2001.00810.x.

(Continued)

*Primary Examiner* — Melur Ramakrishnaiah
(74) *Attorney, Agent, or Firm* — Daniel Morris; Otterstedt & Kammer PLLC

(57) ABSTRACT

A sleeping mask includes a signal processor for processing sensor data, an infrared light source coupled to the signal processor and configured to emit infrared light toward an eyelid of a user, and an array of infrared sensors coupled to the signal processor and configured to receive infrared light reflected from the eyelid of the user.

19 Claims, 10 Drawing Sheets

(51) Int. Cl.
*A61B 5/30* (2021.01)
*A61B 5/369* (2021.01)

(56) References Cited

U.S. PATENT DOCUMENTS

| | | | | |
|---|---|---|---|---|
| 2011/0257712 | A1* | 10/2011 | Wells | A61M 21/00 607/90 |
| 2012/0050668 | A1 | 3/2012 | Howell et al. | |
| 2013/0184516 | A1* | 7/2013 | Genereux | A61M 21/02 600/28 |
| 2014/0169400 | A1* | 6/2014 | Baarman | A61B 5/01 374/45 |
| 2014/0303428 | A1 | 10/2014 | Berka et al. | |
| 2015/0190607 | A1 | 7/2015 | Sugio et al. | |
| 2015/0190650 | A1 | 7/2015 | George | |
| 2016/0022218 | A1* | 1/2016 | Hayes | A61B 5/7275 600/595 |
| 2017/0368297 | A1* | 12/2017 | Tyler | A61N 1/36034 |
| 2019/0224445 | A1* | 7/2019 | Fernandes | A61B 5/163 |
| 2019/0354334 | A1* | 11/2019 | Billinghurst | G06F 3/013 |
| 2020/0129132 | A1* | 4/2020 | Coleman | A61B 5/01 |
| 2020/0268263 | A1* | 8/2020 | Lee | A61B 5/486 |
| 2022/0022809 | A1* | 1/2022 | Bhushan | A61B 5/6822 |

OTHER PUBLICATIONS

Takahashi et al., Precise measurement of individual rapid eye movements in REM sleep of humans, Sleep 20, No. 9, Sep. 1997, pp. 743-752.

Ronald Szymusiak, Body temperature and sleep, chapter 20, Handbook of Clinical Neurology, vol. 156 (3rd series) Thermoregulation: From Basic Neuroscience to Clinical Neurology, Part I, pp. 1-11, Nov. 2018.

Tagluk et al., Estimation of Sleep Stages by an Artificial Neural Network Employing EEG, EMG and EOG, J Med Syst. Apr. 2009, pp. 34:717-725.

Guisle et al., Circadian and sleep/wake-dependent variations in tau phosphorylation are driven by temperature, Sleep Research Society, Nov. 2019, pp. 1-12.

Peter Mell and Timothy Grance, The NIST Definition of Cloud Computing, NIST Special Publication 800-145, Sep. 2011, cover, pp. i-iii and 1-3.

* cited by examiner

SLEEPING MASK METHODS AND PANELS WITH INTEGRATED SENSORS

BACKGROUND

The present invention relates to the electrical, electronic and computer arts, and more specifically, to integrated electronic panels and electronic panel methods.

Sleep is often characterized by one of multiple stages that differ based on characteristics such as brain measurements, body/muscle movement, eye movement, body temperature, heart rate, blood pressure, and the like. Rapid eye movement (REM), for example, is often considered a reliable measurement to identify the REM sleep stage of an individual.

A variety of tests and monitoring mechanisms are conventionally used to detect the stages of sleep, the quality of sleep, and the like. A polysomnogram is a test conducted on an individual overnight to measure brain activity, breathing activity, and muscle activity during sleep. A multiple sleep latency test for daytime sleepiness measures the speed with which the individual falls asleep during the daytime in a quiet environment. A continuous positive airway pressure (CPAP) device is a therapeutic device to address medical conditions such as sleep apnea. CPAP devices conventionally monitor breathing and measure heart rate, oxygen levels, brain waves, arm and leg movement, and the like.

A conventional approach to monitor eye movement during sleep involves the use of an electroencephalogram (EEG) or electrooculography (EOG) based on bioelectrical potential signals. The EOG relies on multiple on-skin electrodes, which may be interrupted or distorted by poor contact, and are burdensome and disruptive to the user, causing additional signal confounds.

SUMMARY

Principles of the invention provide techniques for a sleeping mask panel with integrated sensors. According to some embodiments of the present invention, a sleeping mask comprises a signal processor for processing sensor data, an infrared light source coupled to the signal processor and configured to emit infrared light toward an eyelid of a user, and an array of infrared sensors coupled to the signal processor and configured to receive infrared light reflected from the eyelid of the user.

In one aspect, an exemplary method includes emitting infrared light on an eyelid of a user, detecting a reflected portion of infrared light at each of a plurality of infrared sensors, analyzing a pattern of signals generated by the plurality of infrared sensors in response to the reflected portion of the infrared light, and identifying a sleep event, including REM and non-REM events, corresponding to the pattern of signals.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments provide one or more of:

a flexible panel for a face mask that integrates sensors, amplifiers, and processors for monitoring a plurality of sleep characteristics;

infrared sensors for detecting eye movement and identifying sleep characteristics;

a skin resistance sensor for measuring the electrical conductance of an individual's skin;

an electroencephalogram (EEG) circuit for detecting electrical activity in an individual's brain and recording brain wave patterns;

a movement sensor for measuring electrical activity by muscles of the skeleton of an individual;

an ultrasonic proximity sensor for detecting muscular movement, including eye movement;

a wireless interface for relaying sensor data to a smart device, cloud server, and the like; and a signal processor for aggregating and summarizing sensor data as edge computing for diagnosis, which can reduce the necessary data streaming requirement.

These and other features and advantages of the present invention will become apparent from the following detailed description of illustrative embodiments thereof, which is to be read in connection with the accompanying drawings.

DETAILED DESCRIPTION

Figure 1:
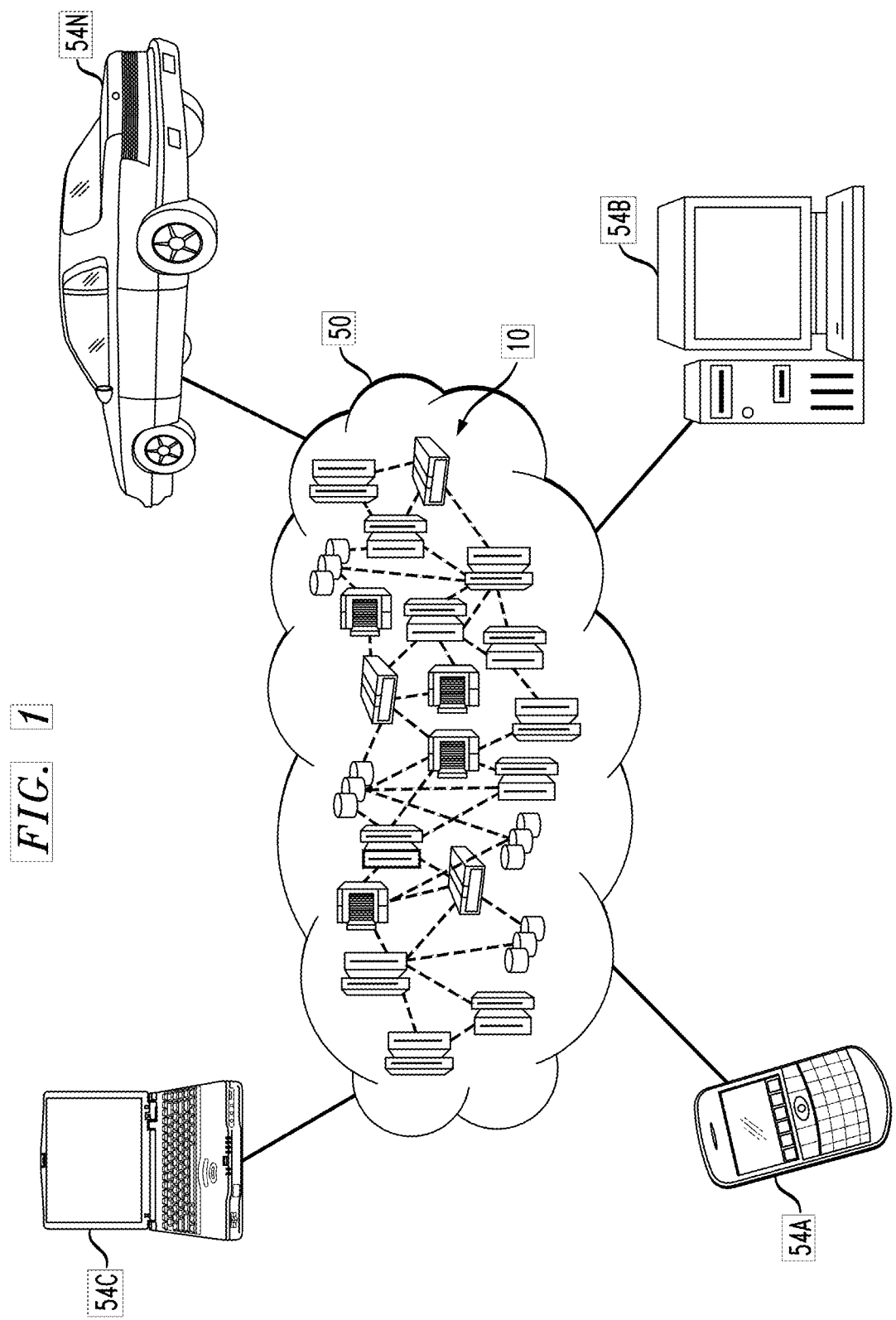
FIG. 1 depicts a cloud computing environment according to an embodiment of the present invention.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
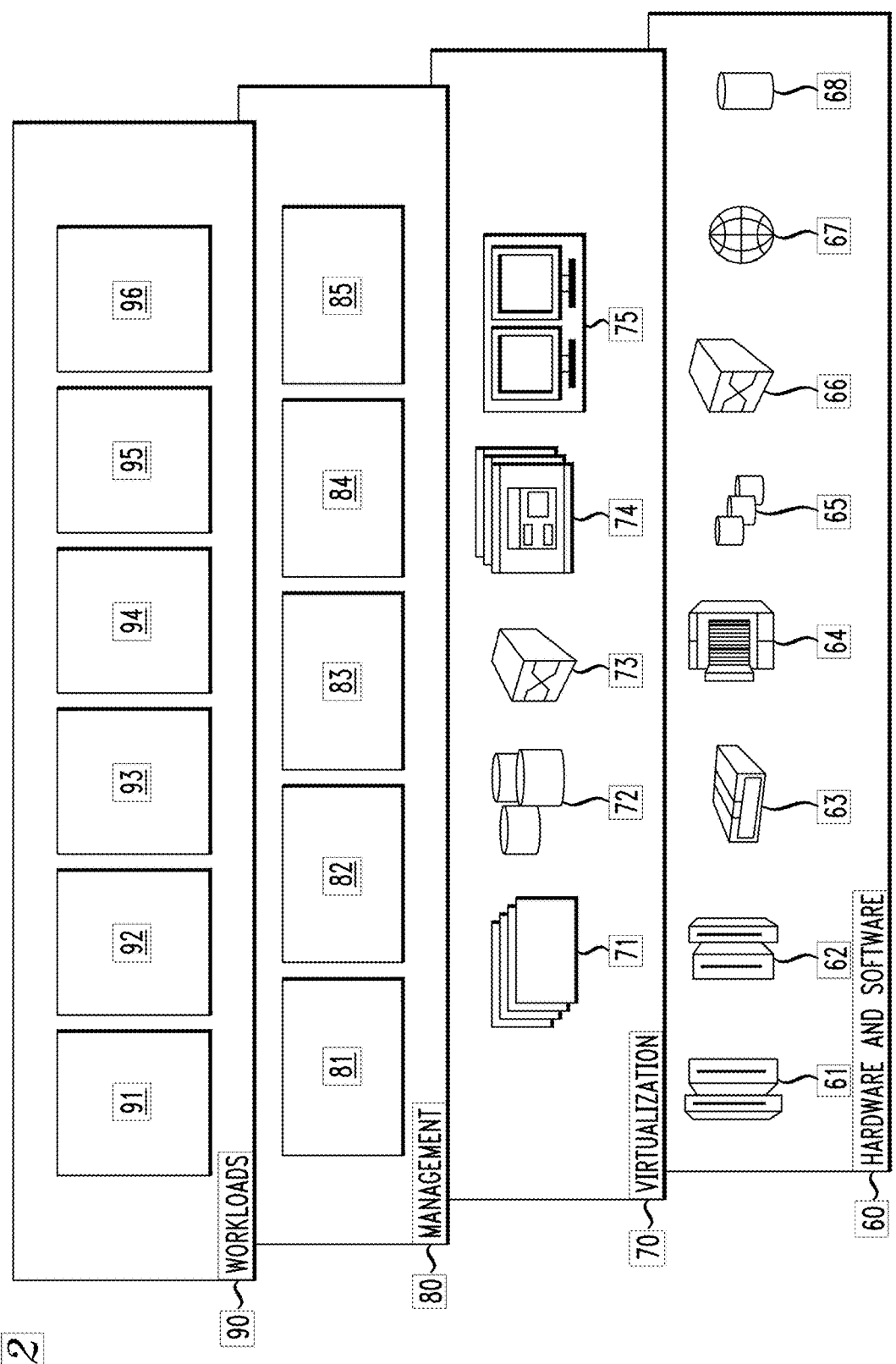
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and sleep analyzer 96.

Figure 3:
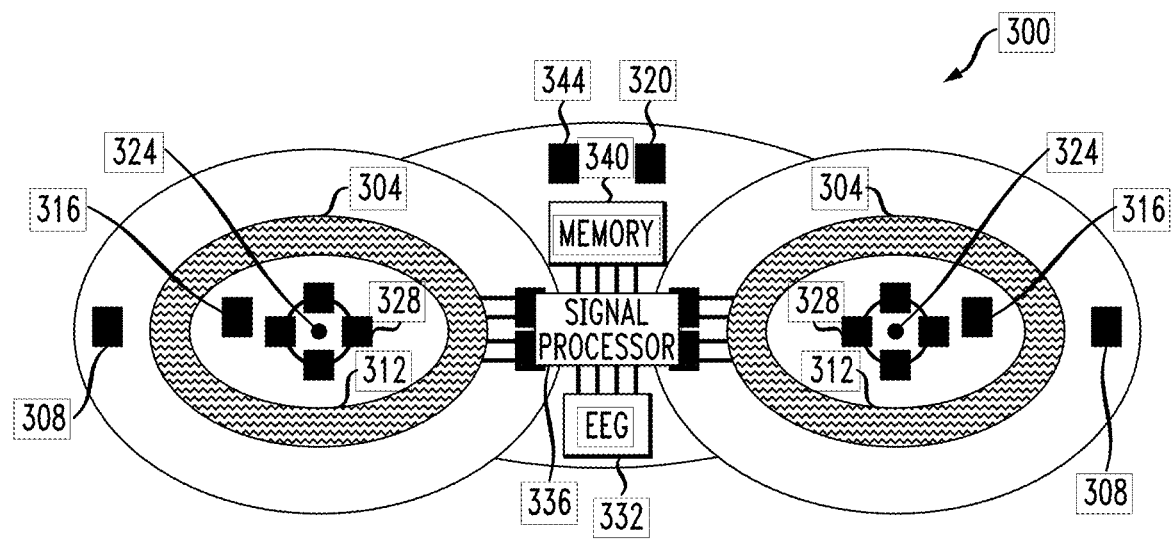
FIG. 3 illustrates an example flexible sleeping mask panel with integrated sensors, amplifiers, and processors, in accordance with an example embodiment.

FIG. 3 illustrates an example flexible sleeping mask panel 300 with integrated sensors, amplifiers, and processors, in accordance with an example embodiment. In one example embodiment, the sleeping mask panel 300 includes a skin resistance sensor 304 (embedded in silicone), electroencephalogram (EEG) leads 308, a movement sensor 312, an ultrasonic proximity sensor 316, a temperature sensor 320, infrared light sources 324, arrays of infrared detectors 328, and an accelerometer 344. An EEG circuit 332 processes signals from the EEG leads 308 to record brain wave patterns of the user. (As used herein, the user is the wearer of the sleeping mask panel 300; individual and user are used interchangeably herein.) A signal processor 336 working in conjunction with a memory/memory card organizer (MCO) 340 processes the recorded brain wave patterns and information obtained from the skin resistance sensor 304, the movement sensor 312, the ultrasonic proximity sensor 316, the temperature sensor 320, and the accelerometer 344. These sensors are used to monitor eye movement, head movement and position, and the like. In one example embodiment, the obtained multimodal sensor data obtained from the sensors is aggregated to build, train, and improve classifiers that detect the stages of sleep, sleep abnormalities, sleep characteristics, and the like. In one example embodiment, the signal processor 336 includes a Bluetooth or other network interface for communicating the sensor data, in raw and/or aggregated form, with a smart device, a network, a cloud server, and the like.

In one example embodiment, the skin resistance sensor 304 measures the electrical conductance of an individual's skin. An individual's sympathetic nervous system is susceptible to strong emotions, such as those encountered during dreaming. This can result, for example, in sweating during sleep which will impact the measured electrical conductance of the user's skin, or may be indicative of important medical symptoms. In one example embodiment, the measured electrical conductance of skin is used as an indication of sweating level.

The EEG circuit 332 processes signals from the EEG leads 308 to detect electrical activity in an individual's brain and to record the brain wave patterns. The brain wave patterns are generated as brain cells communicate with each other via electrical impulses and can be analyzed to identify brain activity and to characterize the individual's sleep.

Each movement sensor 312 detects movement of the skeletal muscles of an individual. Each movement sensor 312 may be implemented by a piezoelectric film sensor, a flexible capacitive sensor, or similar device. A piezoelectric film sensor measures electrical activity by muscles of the skeleton of an individual (known as electromyography). In one example embodiment, the electrical activity is used to produce an electromyogram. A capacitive sensor measures the dielectric of a nearby entity, such as air, the skin of an individual, and the like. For example, it can detect muscle movement of an individual by detecting a change in the measured bioelectrical potential. The movement sensor(s) 312 may be installed on the sleeping mask panel 300, the soft body of the mask, the soft eyepieces of the mask, or any combination thereof.

The ultrasonic proximity sensor 316 provides accurate distance measurement from the perspective of the ultrasonic proximity sensor 316. In one example embodiment, the ultrasonic proximity sensor 316 is used to detect eye movement. In one example embodiment, the ultrasonic proximity sensor 316 is used in conjunction with the arrays of infrared detectors 328 to provide a more meaningful mapping of eye motion by increasing the accuracy of the detection.

The temperature sensor 320 detects the body temperature of the individual wearing the sleeping mask panel 300. An individual's body temperature is indicative of the REM vs. non-REM sleep stages being experienced by the user, the sleep quality, and the like. For example, within a sleep episode, patterns of autonomic nervous system and thermoeffector activity, and the ability to defend against heat and cold exposure differ during nonrapid eye movement (NREM) and rapid eye movement (REM) sleep.

The infrared light sources 324 and the arrays of infrared detectors 328 are used to detect eye movement of the user. Eye movement is indicative of an individual's quality of sleep, REM or non-REM sleep, and the like, as described more fully below in conjunction with FIGS. 5A and 5B.

Figure 4:
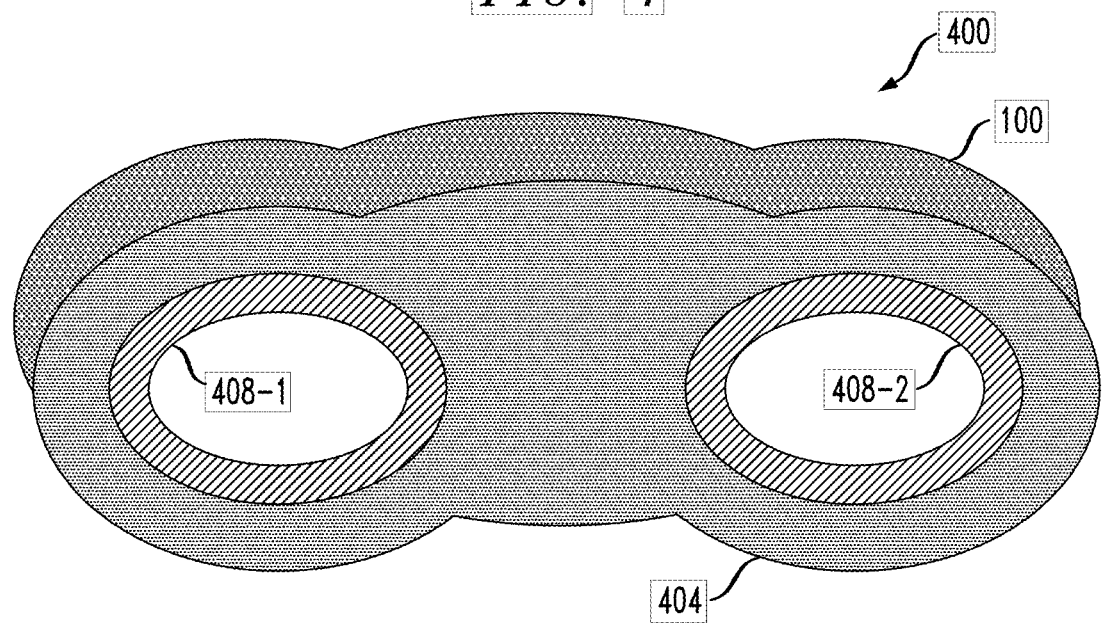
FIG. 4 illustrates a soft mask overlaid on the flexible sleeping mask panel, in accordance with an example embodiment.

FIG. 4 illustrates a soft mask 400 overlaid on the flexible sleeping mask panel 100, in accordance with an example embodiment. The soft mask 400 comprises a soft body 404 and two soft eyepieces 408-1, 408-2. In one example embodiment, the soft body 404 and the soft eyepieces 408-1, 408-2 are composed of materials such as fabric stuffed with cotton, sponge, and the like. In one example embodiment, the soft eyepieces 408-1, 408-2, or portions of the soft eyepieces 408-1, 408-2, are embedded with metal particles to create electrical conductivity such that each soft eyepiece 408-1, 408-2 can function as a component of a sensor (such as an EEG lead 308) and the like. Each eyepiece 408-1, 408-2 encompasses a cut-out within the soft body 404 that exposes the infrared light sources 324 and the arrays of infrared detectors 328. Other sensors, such as the temperature sensor 320, the EEG leads 308, and the like, may be exposed to the user by being embedded in the fabric of the soft body 404 and/or the two soft eyepieces 408-1, 408-2, or via cut-outs within the soft body 404.

Figure 5A:
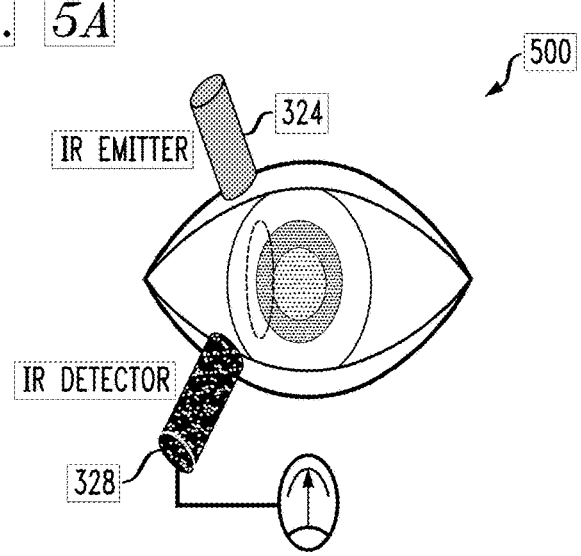
FIG. 5A illustrates the spatial relationship between each infrared light source and one sensor of the array of infrared detectors.
Figure 5B:
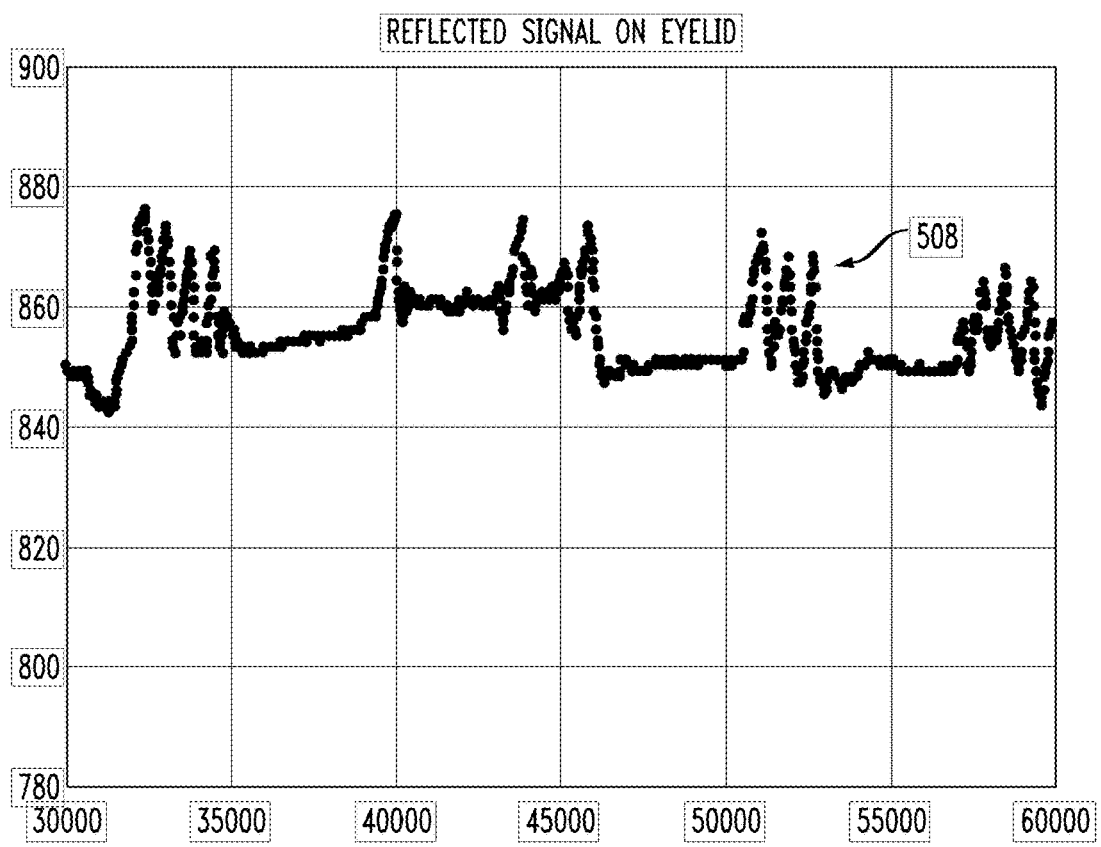
FIG. 5B is a waveform of an example signal received by the infrared detector while an individual periodically rolls an eyeball, in accordance with an example embodiment.

FIG. 5A illustrates the spatial relationship between each infrared light source 324 and one sensor of the array of infrared detectors 328, in accordance with an example embodiment. In one example embodiment, the infrared light source 324 shines infrared light on an eyelid of an individual. The infrared light is reflected by the eyelid to each sensor of the corresponding array of infrared detectors 328. Movement of the individual's eyeball will cause movement of the eyelid that will be detected as a change in the amount of reflected light received by each infrared sensor. The frequency and pattern of such movement is analyzed to characterize, for example, REM and non-REM stages of sleep of the user. FIG. 5B is graph 504 a waveform 508 of an example signal received by a sensor of the infrared detector 328 while an individual periodically rolls an eyeball. By aggregating data from multiple sensors of the arrays of infrared detectors 328, the direction and frequency of the movement of the eyeball can be detected. In one example embodiment, as the infrared light is shone toward the closed eye lids, the reflected light signal is captured by each sensor of the infrared detector 328. The reflected light intensity changes when an eye lid deforms due to eyeball movement. The eyeball movement in the horizontal and vertical directions is then detected and characterized using differential signal processing.

Figure 6:
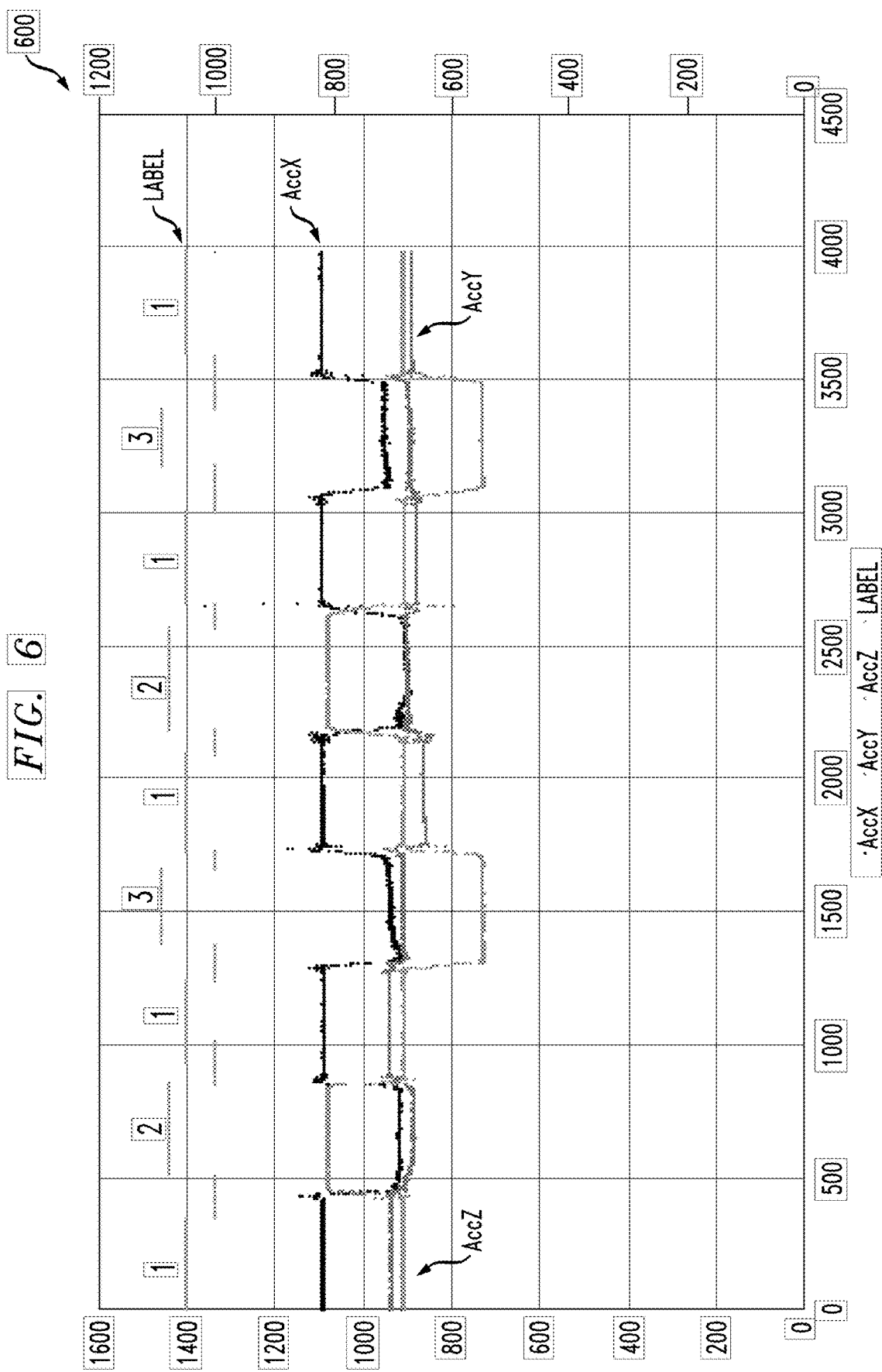
FIG. 6 illustrates the waveforms for the x, y, and z axis produced by an accelerometer integrated into the flexible sleeping mask panel, in accordance with an example embodiment.

FIG. 6 is a graph 600 illustrating the waveforms for the x 604, y 608, and z 612 axis produced by the accelerometer integrated into the flexible sleeping mask panel 300, in accordance with an example embodiment. The output of the accelerometer is used to determine the position of the individual's head: facing up, facing left, and facing right. By analyzing the waveforms, a configuration is identified: configuration #1 of the waveforms indicates that the individual's head is facing up, configuration #2 of the waveforms indicates that the individual's head is facing left, and configuration #3 of the waveforms indicates that the individual's head is facing right. In one example embodiment, machine learning is used to detect and identify a head motion event, such as an individual turning in a left or a right direction (while lying down), an individual facing in a left or a right direction, and the like.

Figure 7:
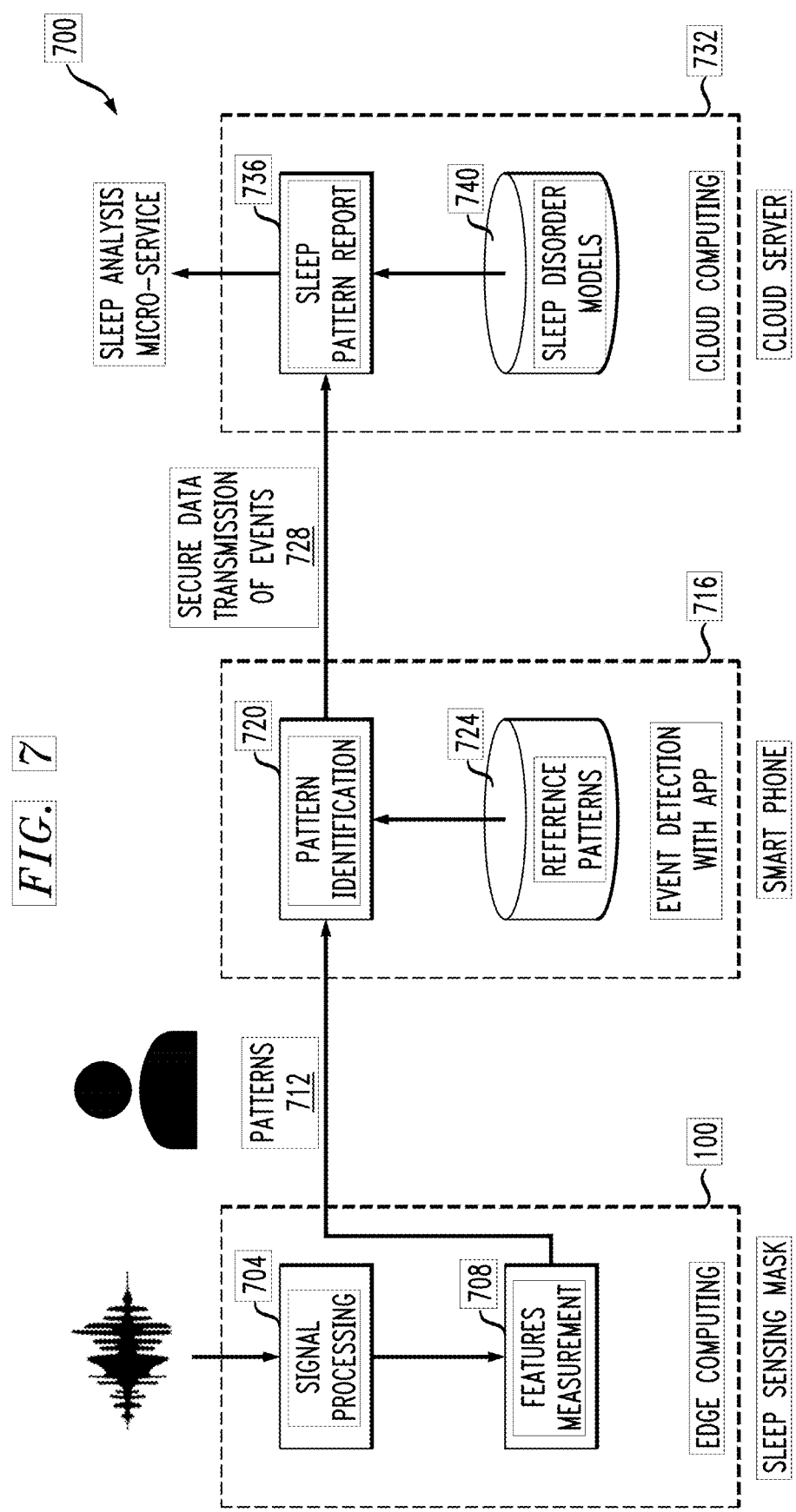
FIG. 7 is a block diagram of an example system for performing pre-processing of the sensor data for a sleeping mask panel, in accordance with an example embodiment.

FIG. 7 is a block diagram of an example system 700 for performing pre-processing of the sensor data for the sleeping mask panel 100, in accordance with an example embodiment. In one example embodiment, signals from the sensors of the sleeping mask panel 100 are subjected to signal processing 704 and features measurement 708 by the signal processor 336 to generate patterns 712. It should be understood that the signal processing 704 can include one or more of an analog-to-digital conversion, filtering (high-pass or low-pass), etc., as may be needed to condition the signal for feature measurement 708. The generated patterns 712 are transferred to, for example, a smart phone 716 or similar device. The smart phone 716 performs pattern identification 720 on the received patterns 712 by comparing each generated pattern 712 to a database of reference patterns 724 associated with known events. Based upon the comparison, the smart phone 716 detects events 728, such as a user's rapid eye movement and the presence of REM sleep for the individual. The events 728 are securely transmitted to a cloud server 732. The events 728 are aggregated and summarized by the cloud server 732 and a sleep pattern report 736 is produced based on a database of sleep disorder models 740. For example, REM sleep may be detected by analyzing the events 728. In one example embodiment, the performance of the pattern identification 720 on the received patterns 712 (by comparing each generated pattern 712 to a database of reference patterns 724) and the detection of the events 728 is performed by the signal processor 336.

Figure 8:
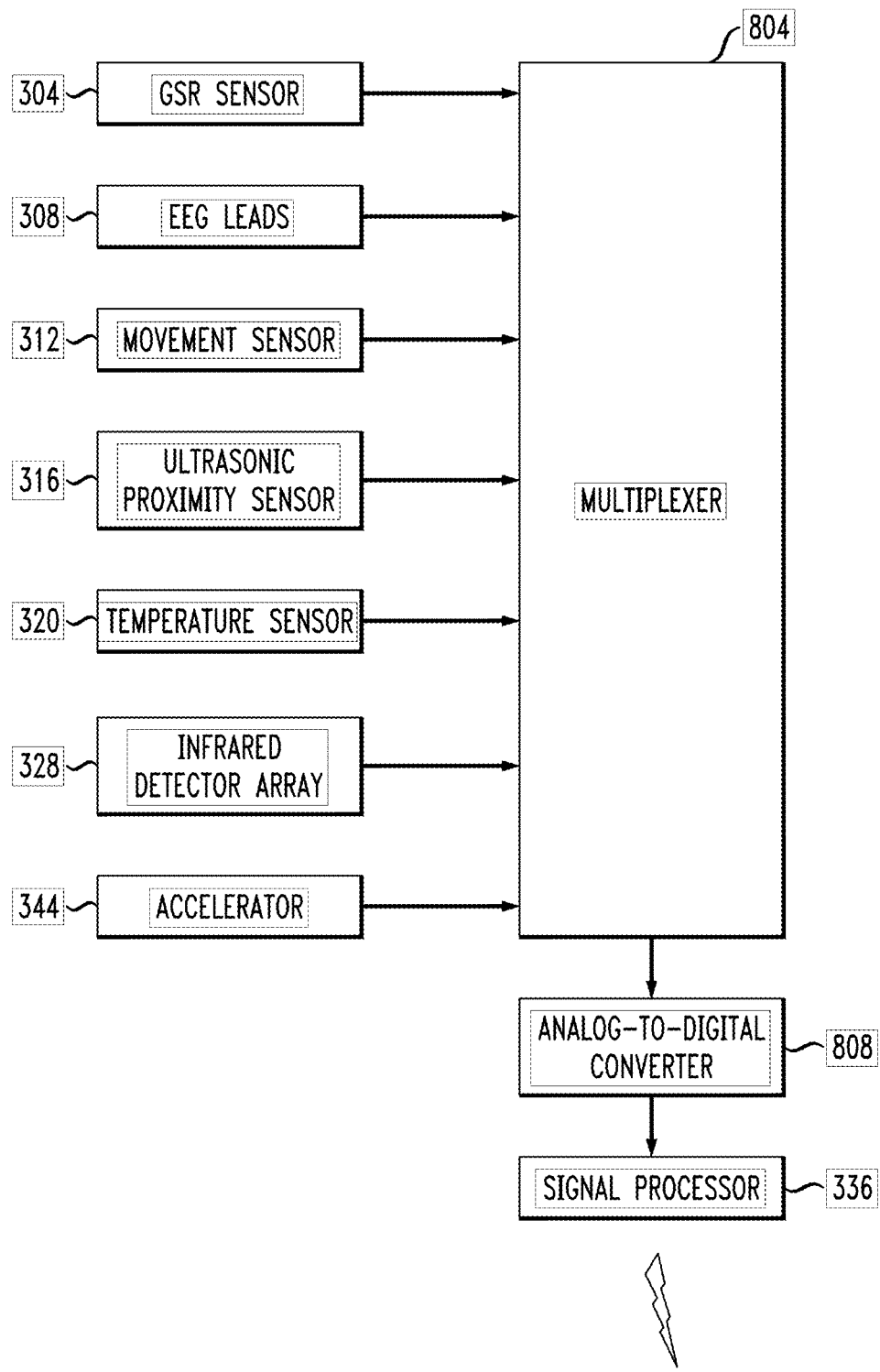
FIG. 8 is a block diagram of a sleeping mask panel, in accordance with an example embodiment.

FIG. 8 is a block diagram of the sleeping mask panel 300, in accordance with an example embodiment. In one example embodiment, the outputs of the skin resistance sensor 304, the EEG leads 308, the movement sensor 312, the ultrasonic proximity sensor 316, the temperature sensor 320, the infrared light source 324, the array of infrared detectors 328, and the accelerometer are coupled to a multiplexer 804 that enables the signal processor 336 to select one of the sensor output signals. In one example embodiment, the output of the multiplexer 804 is coupled to an analog-to-digital converter (ADC) 808 and the output of the ADC 808 is coupled to the signal processor 336, enabling the signal processor 336 to read the digital value of the signal provided by the corresponding sensor. As described above, the signals from the sensors of the sleeping mask panel 300 are subjected to signal processing 704 and features measurement 708 by the signal processor 336 to generate the patterns 712. In one example embodiment, the signal processor 336 uses an integrated Bluetooth interface to transmit the patterns 712 to, for example, the smart phone 516 or a similar device.

Figure 9:
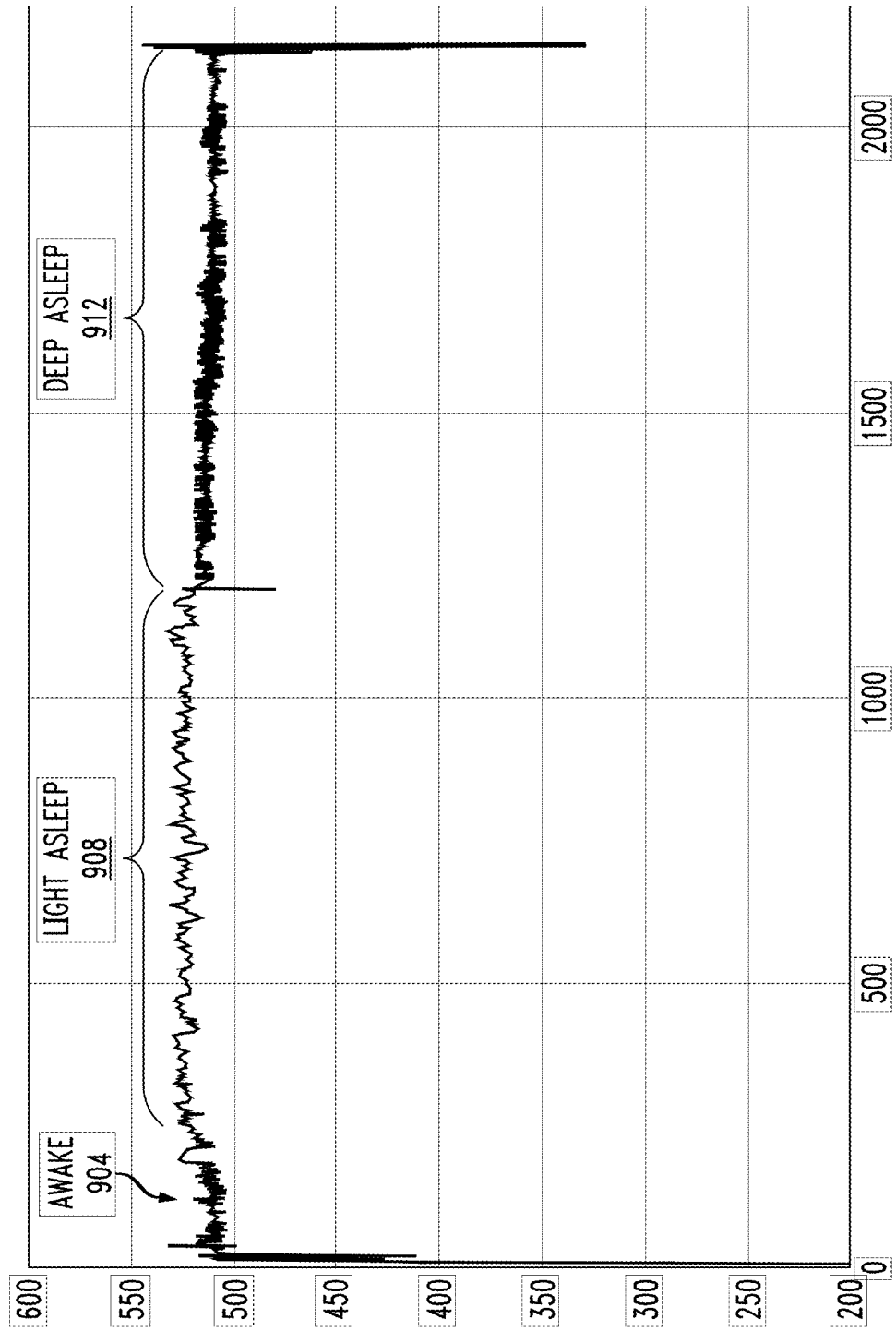
FIG. 9 is a waveform of an example signal from a sensor of the array of infrared detectors, in accordance with an example embodiment.

In one example embodiment, each sensor is periodically read to detect activity or an event corresponding to the sensed sleep characteristic. Once an event or other activity is detected, more extensive measurements may be initiated. For example, since REM sleep is characterized by eye movement at a typical frequency of approximately 16 times per minute, or one event every four seconds, the movement sensor 312 may be read every 500 millisecond (msec) once eye movement is first detected. FIG. 9 is a waveform of an example signal from a sensor of the array of infrared detectors 328, in accordance with an example embodiment. As illustrated in FIG. 9, the waveform (e.g., measured in milli-volts) can be analyzed to identify the stage of sleep, such as a REM stage or a non-REM stage (where the x-axis represents the voltage and the y-axis represents time). The segment 904 corresponds to an "awake" period of time, segment 908 corresponds to a period of light sleep, and segment 912 corresponds to a period of deep sleep.

In one example embodiment, cluster solutions for feature dynamic groupings of a sample of data across time are combined with a priori knowledge of sleep stages and assigned to a particular stage. An unsupervised algorithm would add individual characteristics for more precise individual predictions. Machine learning and training can improve accuracy of detecting.

In one example embodiment, a sleeping mask 300 is operated by emitting infrared light toward a closed eye lid, detecting a reflected portion of infrared light at each of a plurality of infrared sensors 328, 704, 708; analyzing a pattern 712 of signals generated by the plurality of infrared sensors 328 in response to the reflected portion of the infrared light 720; identifying a sleep event corresponding to the pattern 712 of signals 720, 736; detecting an insufficient amount of REM sleep 720, 736; and generating an alert identifying the detection of the insufficient amount of REM sleep 736.

In one aspect, a sleeping mask 300 comprising a signal processor 336 for processing sensor data 704, detecting an insufficient amount of REM sleep 720, 736, and generating an alert identifying the detection of the insufficient amount of REM sleep 736; an infrared light source coupled to the signal processor 336 and configured to emit infrared light toward an eyelid of a user; and an array of infrared sensors 328 coupled to the signal processor 336 and configured to receive infrared light reflected from the eyelid of the user.

In one aspect, a non-transitory computer readable medium comprises computer executable instructions which when executed by a computer cause the computer to perform the method of emitting infrared light on an eyelid of a user; detecting reflected infrared light at each of a plurality of infrared sensors 328, 704, 708; analyzing a pattern 712 of signals generated by the plurality of infrared sensors 328 in response to the reflected infrared light; identifying a sleep event corresponding to the pattern 712 of signals; detecting an insufficient amount of REM sleep 720, 736; and generating an alert identifying the detection of the insufficient amount of REM sleep 736.

In one example embodiment, the sleep event is a detection of a rapid eye movement (REM) of the user during sleep. In one example embodiment, the identification of the sleep event is based on a body temperature of the user. In one example embodiment, the identification of the sleep event is based on muscle movement of the user. In one example embodiment, the identification of the sleep event is based on a measured electrical resistance of skin of the user. In one example embodiment, the identification of the sleep event is based on one or more measurements of an accelerometer 344. In one example embodiment, the identification of the sleep event is based on one or more measurements of an ultrasonic proximity sensor 316.

In one example embodiment, the sleeping mask further includes a plurality of electroencephalogram (EEG) sensors 308 configured to measure brain waves of the user. In one example embodiment, the sleeping mask further includes a piezoelectric sensor film 312 configured to detect muscle movement of the user. In one example embodiment, the sleeping mask further includes a capacitive sensor 312 configured to detect muscle movement of the user. In one example embodiment, the sleeping mask further includes a multi-point temperature sensor 320 configured to measure a body temperature of the user. In one example embodiment, the sleeping mask further includes a skin resistance sensor 304 configured to measure a skin resistance of the user. In one example embodiment, the signal processor 336 is configured to aggregate and summarize the sensor data. In one example embodiment, the infrared light source and the array of infrared sensors 328 are mounted on a circuit board. In one example embodiment, the circuit board is a flexible circuit board. In one example embodiment, the sleeping mask further includes an accelerometer 344 (e.g., located in the sleeping mask, approximately between the user's eyes) that obtains one or more measurements of acceleration. In one example embodiment, the sleeping mask further includes an ultrasonic proximity sensor 316 to measure a distance to an object.

Figure 10:
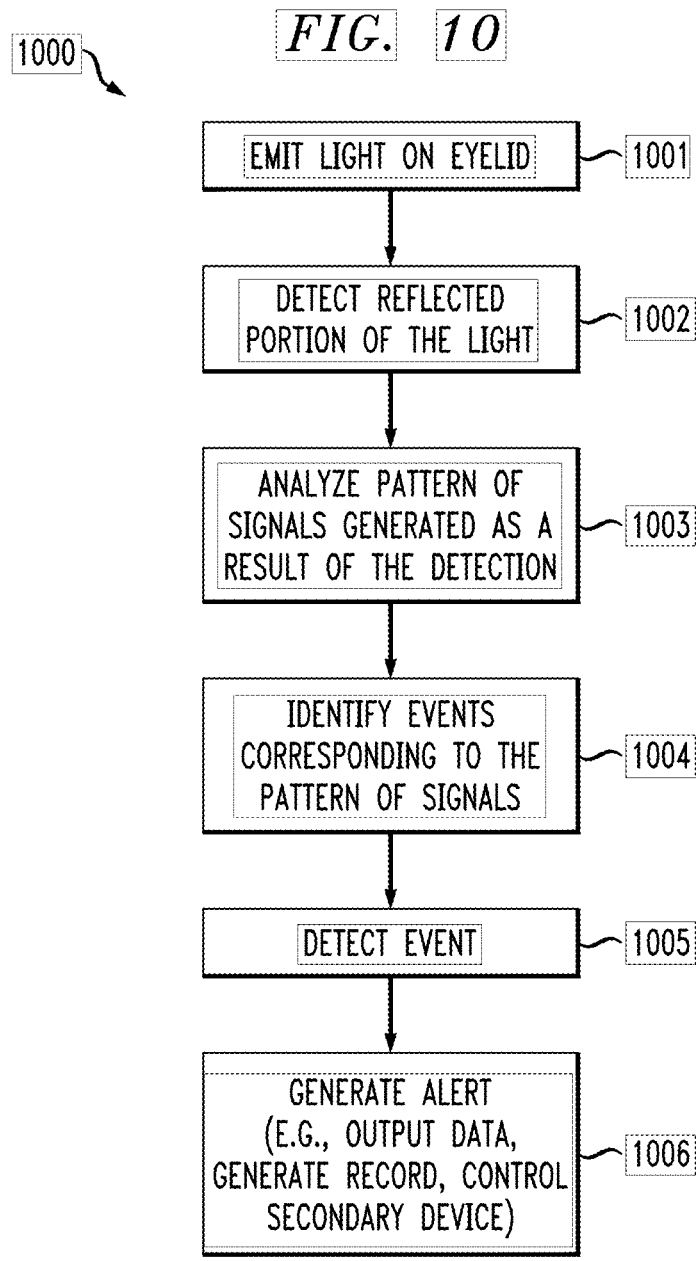
FIG. 10 is a flow diagram of a method in accordance with an example embodiment.

According to some embodiments and referring to FIG. 10, a method (1000) includes emitting infrared light on an eyelid of a user (1001), detecting a reflected portion of the infrared light at each of a plurality of infrared sensors (1002), analyzing a pattern of signals generated by the plurality of infrared sensors in response to the reflected portion of the infrared light (1003), identifying a sleep event corresponding to the pattern of signals (1004), detecting an insufficient amount of rapid eye movement (REM) sleep (1005), and generating an alert identifying the detection of the insufficient amount of REM sleep (1006).

According to some embodiments, the system generates an alert (at block 1006) to a clinician (i.e., a device available to the clinician) associated with the user's care. When the system detects outlier events for certain prespecified features related to a condition, it generates the alert to the user and/or to the clinician. According to some embodiments, in the case of sleep apnea, if the system detects loud snoring (e.g., using a microphone), an electronic signal is generated that marks a presence (e.g., in a data record output by the system, which can be electronic or printed on a physical media such as a paper chart role) of the observation to the user.

According to some embodiments, the system detects (at block 1006) (e.g., for a given condition) a level of severity, classification, or state based on an assessment of values produced by the sensors. This detection can be based on real-time or historic values. According to some embodiments, the detection is documented in electronic records in the form of data or graphs as evidence of a health event, and provides information to the user in order to meet their own goals or adjust health-related behavior, or to send the data to a clinician who may aid in producing a diagnosis or treatment plan. According to one or more embodiments, and in the case of sleep apnea, the system detects that a length of REM sleep is different from a length of REM sleep observed in prior nights (e.g., it is entirely absent, two standard deviations below normal, etc.). The system generates a time series graph recording the event and a classification (e.g., aberrant, serious, etc.) in the observed sensor values relative to the prior observations.

According to some embodiments, the system (at block 1006) communicates an electronic signal (e.g., output) to a secondary device, causing the secondary device to take an action. For example, the secondary device is caused to update settings on medical hardware based on a prespecified or classified event detected by the system and communicated to the secondary device at block 1006. The update can include changing a dosage of a medication (e.g., administrated by a smart intravenous drip device), or settings on a nighttime ventilator. In the sleep apnea example, if the sensors detect major respiratory changes, including dangerous prolonged intervals between breathing, alterations to device settings are triggered to updated settings (e.g., for pressurized air, etc.), or a tone alert to wake the user.

Figure 11:
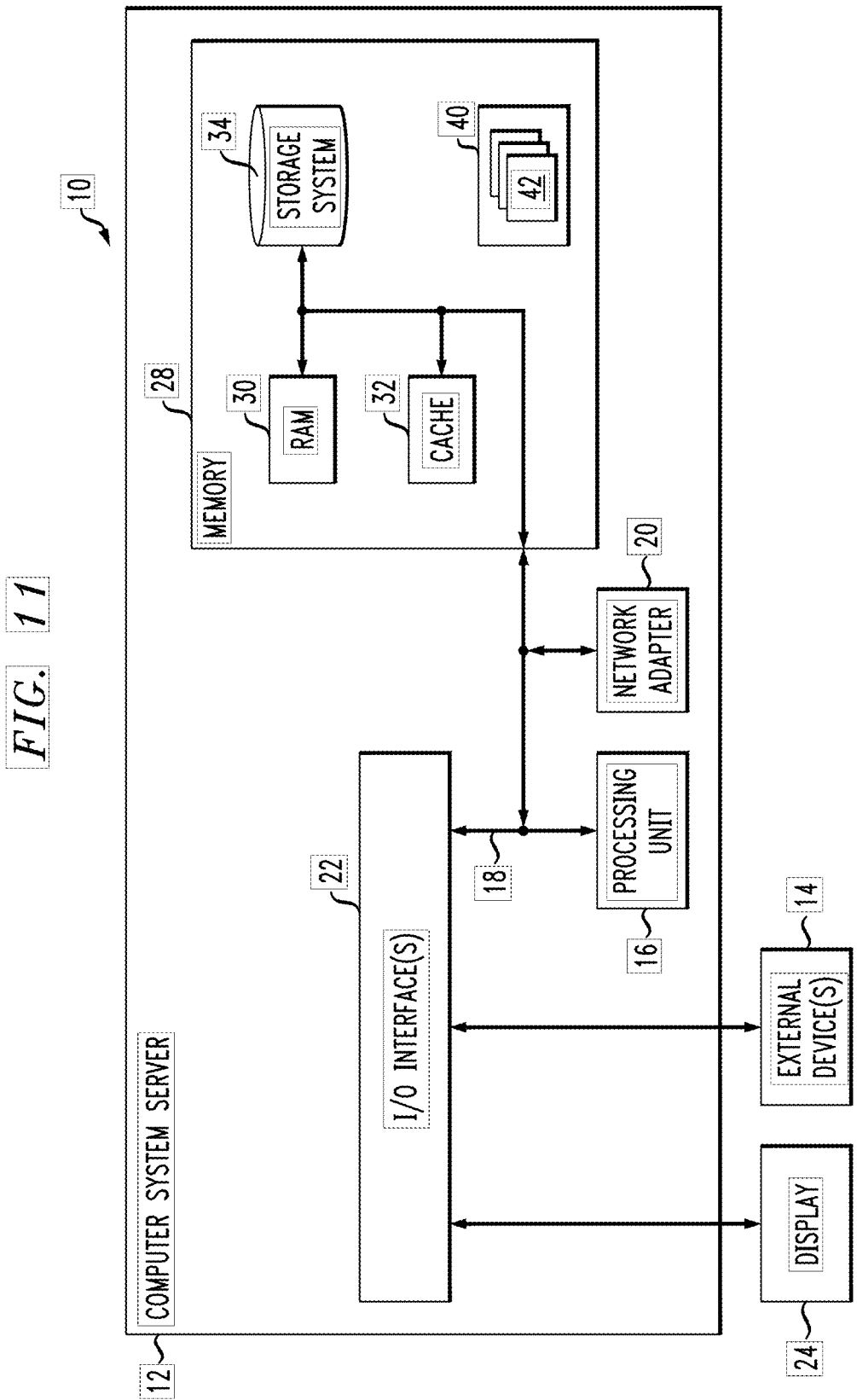
FIG. 11 depicts a computer system that may be useful in implementing one or more aspects and/or elements of the invention, also representative of a cloud computing node according to an embodiment of the present invention.

One or more embodiments of the invention, or elements thereof, can be implemented in the form of an apparatus including a memory and at least one processor that is coupled to the memory and operative to perform exemplary method steps. FIG. 11 depicts a computer system that may be useful in implementing one or more aspects and/or elements of the invention, also representative of a cloud computing node according to an embodiment of the present invention. Referring now to FIG. 11, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/ server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 11, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 11, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 6) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 1-2 and accompanying text.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    emitting infrared light on an eyelid of a user;
    detecting a reflected portion of the infrared light at each of a plurality of infrared sensors;
    analyzing a pattern of signals generated by the plurality of infrared sensors in response to the reflected portion of the infrared light, the analyzing being performed by comparing the generated pattern of signals to a database of reference patterns associated with known events;
    identifying a sleep event corresponding to the pattern of signals;
    detecting an insufficient amount of rapid eye movement (REM) sleep; and
    generating an alert identifying the detection of the insufficient amount of REM sleep.

2. The method of claim 1, wherein the sleep event is a detection of a rapid eye movement of the user during sleep.

3. The method of claim 1, wherein the identification of the sleep event further comprises detecting a body temperature of the user.

4. The method of claim 1, wherein the identification of the sleep event further comprises detecting muscle movement of the user.

5. The method of claim 1, wherein the identification of the sleep event further comprises measuring an electrical resistance of skin and a corresponding amount of sweat of the user.

6. The method of claim 1, wherein the identification of the sleep event further comprises detecting one or more measurements of an accelerometer.

7. The method of claim 1, wherein the identification of the sleep event further comprises detecting one or more measurements of an ultrasonic proximity sensor.

8. A sleeping mask comprising:
    a signal processor for processing sensor data;
    an infrared light source coupled to the signal processor and configured to emit infrared light toward an eyelid of a user;
    a galvanic skin response sensor configured to measure a skin resistance and a corresponding amount of sweat of the user; and
    an array of infrared sensors coupled to the signal processor and configured to receive infrared light reflected from the eyelid of the user, the signal processor configured to analyze a pattern of signals generated by the array of infrared sensors in response to a reflected portion of the infrared light, the analyzing being performed by comparing the generated pattern of signals to a database of reference patterns associated with known events.

9. The sleeping mask of claim 8, further comprising:
    a plurality of electroencephalogram (EEG) sensors configured to measure brain waves of the user.

10. The sleeping mask of claim 8, further comprising:
    a piezoelectric sensor film configured to detect muscle movement of the user.

11. The sleeping mask of claim 8, further comprising:
    a capacitive sensor configured to detect muscle movement of the user.

12. The sleeping mask of claim 8, further comprising:
    a multi-point temperature sensor configured to measure a body temperature of the user.

13. The sleeping mask of claim 8, wherein the signal processor is configured to aggregate and summarize the sensor data.

14. The sleeping mask of claim 8, wherein the signal processor, the infrared light source and the array of infrared sensors are mounted on a circuit board.

15. The sleeping mask of claim 14, wherein the circuit board is a flexible circuit board.

16. The sleeping mask of claim 8, further comprising an accelerometer to obtain one or more measurements of acceleration.

17. The sleeping mask of claim 8, further comprising an ultrasonic proximity sensor to measure a distance to an object.

18. A non-transitory computer readable medium comprising computer executable instructions which when executed by a computer cause the computer to perform the method of:
  emitting infrared light on an eyelid of a user;
  detecting a reflected portion of the infrared light at each of a plurality of infrared sensors;
  analyzing a pattern of signals generated by the plurality of infrared sensors in response to the reflected portion of the infrared light, the analyzing being performed by comparing the generated pattern of signals to a database of reference patterns associated with known events;
  identifying a sleep event corresponding to the pattern of signals;
  detecting an insufficient amount of rapid eye movement (REM) sleep; and
  generating an alert identifying the detection of the insufficient amount of REM sleep.

19. The non-transitory computer readable medium of claim 18, wherein the sleep event is a detection of a rapid eye movement of the user during sleep.

\* \* \* \* \*